United States Patent
Kishino et al.

(10) Patent No.: US 6,472,366 B2
(45) Date of Patent: Oct. 29, 2002

(54) HEPATOCYTE GROWTH FACTOR FOR TREATMENT OF DIABETES

(75) Inventors: Michiko Kishino, Suita; Chikao Nakayama, Sanda; Mutsuo Taiji; Junji Ichihara, both of Takatsuki; Hiroshi Noguchi, Kawanishi, all of (JP)

(73) Assignee: Sumitomo Pharmaceuticals Company, Limited, Osaka-fu (JP)

( * ) Notice: Subject to any disclaimer, the term of this patent is extended or adjusted under 35 U.S.C. 154(b) by 0 days.

(21) Appl. No.: 10/055,380

(22) Filed: Jan. 25, 2002

(65) Prior Publication Data

US 2002/0122829 A1 Sep. 5, 2002

Related U.S. Application Data

(62) Division of application No. 09/355,098, filed as application No. PCT/JP98/00157 on Jan. 19, 1998, now Pat. No. 6,391,312.

(30) Foreign Application Priority Data

| Jan. 23, 1997 | (JP) | 9/26111 |
| Apr. 4, 1997 | (JP) | 9/102478 |
| Apr. 4, 1997 | (JP) | 9/102479 |

(51) Int. Cl.$^7$ ......................... A61K 39/00; A01N 37/18
(52) U.S. Cl. ........................................ 514/2; 424/198.1
(58) Field of Search .................. 424/198.1; 514/2, 514/12, 21, 4

(56) References Cited

U.S. PATENT DOCUMENTS

| 5,180,820 A | 1/1993 | Barde et al. |
| 5,438,121 A | 8/1995 | Barde et al. |
| 5,470,582 A | 11/1995 | Supersaxo et al. |
| 5,571,787 A | 11/1996 | O'Brian et al. |
| 5,589,451 A | 12/1996 | Wilson |
| 5,639,275 A | 6/1997 | Baetge et al. |
| 5,783,556 A * | 7/1998 | Clark et al. ..................... 514/4 |

FOREIGN PATENT DOCUMENTS

| JP | 5161493 | 6/1993 |
| JP | 5504965 | 7/1993 |
| JP | 7509600 | 10/1995 |
| WO | WO91/03568 A1 | 3/1991 |
| WO | WO91/03569 A1 | 3/1991 |
| WO | WO92/05254 A1 | 4/1992 |
| WO | WO93/25684 A1 | 12/1993 |
| WO | WO98/22128 A1 | 5/1998 |

OTHER PUBLICATIONS

Liu et al. In Vivo and in Vitro Evidence for Increased Expression of HGF Receptor in Kidney of Diabetic Rat; American Journal of Physiology–Renal Fluid and Electrolyte Physiology, (1996), vol.40, No. 6, pp. F1202–F1210.*

Henderson et al. J. Clin. Inves., vol. 93, pp. 2632–2638, (1994).

Fantuzzi et al., Cytokine, vol. 7, No. 2, pp. 150–156, (Feb. 1995).

(List continued on next page.)

*Primary Examiner*—Jon P. Weber
*Assistant Examiner*—Patricia A Patten
(74) *Attorney, Agent, or Firm*—Birch, Stewart, Kolasch & Birch, LLP

(57) ABSTRACT

The present invention provides a therapeutic agent for treatment of diabetes and hyperlipemia, especially a therapeutic agent for treatment of type II diabetes mellitus, which comprises as the active ingredient a neurotrophic factor such as BDNF (brain-derived neurotrophic factor), ligands of trkB or trkC receptors, NGF, NT-3, NT-4/5, CNTF, GDNF, HGF, etc. Different from conventional oral hypoglycemic agents being mainly used in the treatment of type II diabetes mellitus, the agent of the present invention exhibit blood lipid regulating effects and body fat accumulation regulating effects, in addition to the blood glucose regulating effects. Thus, the agent of the present invention are novel, and can reduce the risk factors in diabetes accompanied by hyperlipemia or obesity, without using any other agent.

4 Claims, 3 Drawing Sheets

*excluding two cases (non detective)
**P<0.01 vs. db/m+PBS
P<0.01 vs. db/db+PBS (t-test)

OTHER PUBLICATIONS

Pelleymounter et al., Experimental Neurology, vol. 131, pp. 229–238, (1995).

Henderson et al., Cytokine, vol. 8, No. 10, pp. 784–793, (Oct. 1996).

Gloaguen et al., Proc. Natl. Acad. Sci., USA, vol. 94, pp. 6456–6561, (Jun. 1997).

Ono et al., Biochemical and Biophysical Research Communications, vol.238, pp. 633–637, (1997).

Apfel et al., Brain Research, vol. 634, pp. 7–12, (1994).

Diabetes Care, vol. 15(12), pp. 1902–1925, (Dec. 1992).

Baillieres Clinical Neurology, vol. 4(3), pp. 593–606, (Nov. 1995).

Yoshiko Furukawa, Journal of Japanese Biochemical Society, vol. 1, No. 68, pp. 14–30.

D.R. Tomlinson, Philos. Trans. R. Soc. London Ser., vol. 351, No. 1338, pp. 455–462.

Lara T. Daniels, Molecular Brain Research, vol. 21, No. 1–2, pp. 171–175, (1993).

* cited by examiner

\*\*P<0.01 vs. db/m+PBS
P<0.01 vs. db/db+PBS (t-test)

*excluding two cases (non detective)

\*\*P<0.01 vs. db/m+PBS
P<0.01 vs. db/db+PBS (t-test)

HEPATOCYTE GROWTH FACTOR FOR TREATMENT OF DIABETES

This application is a divisional of application Ser. No. 09/355,098, filed on Jul. 23, 1999, now U.S. Pat. No. 6,391,312 issued May 21, 2002, and for which priority is claimed under 35 U.S.C. § 120. Application Ser. No. 09/355,098 is the national phase of PCT International Application No. PCT/JP98/00157 filed on Jan. 19, 1998 under 35 U.S.C. § 371. The entire contents of each of the above-identified applications are hereby incorporated by reference. This application also claims priority of Application No. 26111/1997; 102478/1997 and 102479/1997 filed in JAPAN on Jan. 23, 1997; Apr. 4, 1997 and Apr. 4, 1997 (respectively) under 35 U.S.C. § 119.

TECHNICAL FIELD

The present invention relates to a therapeutic agent for treating a patient of diabetes or hyperlipemia, more particularly, a therapeutic agent for treating a patient of diabetes or hyperlipemia which comprises a neurotrophic factor as an active ingredient.

BACKGROUND ART

Recently, the number of patients afflicted with degenerative diseases, especially diabetes mellitus, diabetic complications, or hyperlipemia, has been increased, due to an improvement in a living standard, and/or change of the dietary life into the Western style, or increase in lack of exercise. Hyperlipemia is a very important underlining disease, which causes arteriosclerosis, and as a result, further leads to ischemic heart diseases, and occasionally, may lead to the onset of acute pancreatitis. In addition, there is a tendency of increasing numbers of patients afflicted with these diseases in the young generation.

Diabetes is classified into insulin dependent diabetes mellitus (type I, IDDM) and non insulin dependent diabetes mellitus (type II, NIDDM), and more than 90% of patients of diabetes mellitus are patients afflicted with the latter one. Insulin injections are used for the treatment of IDDM, and an oral antidiabetic agent such as sulfonyl urea or a biguanide compound is employed for the treatment of NIDDM, together with exercise therapy or dietary therapy (cf. Today's Therapy 1993, supervised by Shigeaki HINOHARA, Masakazu ABE, published by IGAKU SHOIN, pages 494–498). These drugs are commonly used in order to control the blood glucose level, which is the most important indicator in the treatment of diabetes, but their effects are not sufficient enough, and in fact, continuous hyperglycemia causes various diabetic complications such as diabetic neuropathy, diabetic nephropathy, diabetic retinopathy, diabetic cardiovascular diseases, or delay in healing or ulceration of wound. Besides, various risk factors such as an acute hypoglycemia by insulin injection, prolonged hypoglycemia by an insulin secretagogue, sulfonylurea, lactic acidosis by anaerobic inhibitor of glycolysis, biguanide, affect the quality of life of patients afflicted with diabetes.

In addition, type II diabetes mellitus is often accompanied by hyperlipemia, and an unusual high level of cholesterol or triglyceride (i.e., more than 220 mg/dl of total cholesterol, or more than 150 mg/ml of triglyceride) is a risk factor to cause arteriosclerosis including myocardial infarction, or acute pancreatitis, and hence, it is a target to be treated by medication. In the treatment of hypercholesterolemia, a HMG-CoA reductase inhibitor (e.g., pravastatin, simvastatin), or cholestyramine inhibiting enterohepatic circulation of bile acid is prescribed, and in the treatment of hypertriglyceridemia, a fibrate agent or a nicotinic acid agent having moderate effects is mainly prescribed (cf. Today's Therapy 1993, supervised by Shigeaki HINOHARA, Masakazu ABE, published by IGAKU SHOIN, pp. 515–517; Shoichi BANNO et al, Chiryo (treatment), vol. 78, the extra number, Guideline for Standard Receipt 96, pp. 1060–1066). However, an essential drug therapy for hyperlipemia has not been established yet, and diabetic complications caused by abnormal continuous blood lipid level, such as arteriosclerosis, ischemic heart diseases, are one of the main causes for death in the developed countries. HMG-CoA reductase inhibitors can be orally administered, and have excellent pharmacological activities, but they also show an adverse serious side effect, rhabdomyolysis, in patients of hepatic dysfunction or renal dysfunction.

Type II diabetes mellitus is often accompanied by obesity. Obesity is considered to relate to hypertension, or to the vascular disorders of the brain and the heart, in the epidemiology research, and obesity is mainly treated by a dietary therapy or an exercise therapy. However, in case of advanced obesity or in case that exercise is not available, a surgery (stomach contraction operation) or a medication (central nervous system stimulators such as an adrenergic drug, a serotonin-type drug, a digestive absorption inhibitor) have been employed, but such therapies are still in the trial stage, and an essential drug therapy for obesity has not been established yet (cf. Obesity, Nippon-Rinsho, vol. 53, 1995, special issue, issued on June 22, 1995, pp. 481–492, Nippon Rinsho Co.).

As mentioned above, type II diabetes mellitus, hyperlipemia and obesity are extremely deeply related each other, however, in order to improve each condition, merely a symptomatic therapy or a symptomatic medication has been employed. However, a therapy with a controlled diet or a multiple medication is not preferable because these methods give the patients more burdens.

On the other hand, neurotrophic factors are a generic name of proteins, which are provided from target cells or neurons and glia cells·Schwann cells in the living body, and show activities to maintain the survival and differentiation of neurons, and are classified into many types according to the kinds of nerves or receptors to function. Among them, proteins being known as neurotrophins have high structural homology with each other, and form a family thereof. The typical examples thereof are NGF (nerve growth factor), BDNF (brain-derived neurotrophic factor), NT-3 (neurotrophin 3), NT-4/5, etc., and they are known to act as a specific ligand of receptors, which are the products of P-75 and trk genes (cf. Takeshi NONOMURA, Hiroshi HATANAKA; Jikken Igaku vol. 13, p. 376 (1995)). Neurotrophic factors such as NGF, BDNF, etc. have been studied on the clinical utility thereof as a therapeutic agent for treating a patient of neurodegenerative diseases such as Alzheimer's disease, diabetic neuropathy, ALS, etc., but an activity of reducing blood glucose level in the living body in the state of hyperglycemia or an activity on fat metabolism disorder such as hyperlipemia has not been reported yet. For example, A. P. Mizisin et al. Society for Neuroscience, vol. 21, p. 1535 (1995) discloses the pharmacological activity of BDNF on diabetic peripheral neuropathy, but this literature merely suggests the possible pharmacological activity of BDNF on neuropathy based on the finding that BDNF improves the reduction of motor nerve conduction velocity in vivo, and said literature does not suggest the ameliorating activity of common pathologies of diabetes such as hyperglycemia, or insulin resistance causing hyperglycemia. Japanese Patent Publication No. 7-507053 (WO 93/15608) discloses an effect on diabetic retinopathy as a pharmacological activity of BDNF, but said patent application is related to neuropathy in retina. Besides, activities on hyperlipemia or obesity, which is fat metabolism disorder, and on hyperinsulinemia, which is endocrinopathy, have not been reported as an activity of neurotrophic factors. In addition, hitherto, the hypoglycemic activity of other neurotrophic factors has not been known yet, as mentioned below. That is, Brain Research vol. 634, p. 7–12 (1994) discloses the peripheral dysenthesia improving activity of NGF in streptozotocin-induced diabetic model rats, but its hypoglycemic activity is not disclosed therein. Japanese Patent Publication No. 5-161493 (WO 91/3659) discloses the utility of NT-3 in the case of peripheral neuropathy including diabetic neuropathy, but its hypoglycemic activity is not disclosed therein. In addition, Japanese Patent Publication No. 7-509600 (WO 93/25684) and Japanese Patent Publication No. 6-501617 (WO 92/5254) disclose the utility of NT-4 in the treatment of peripheral neuropathy including diabetic neuropathy, but its hypoglycemic activity is not disclosed therein. However, the hypoglycemic activity of CNTF is disclosed (cf. Cytokine vol. 7, p. 150–156 (1995); Cytokine vol. 8, p. 784–793 (1996)), but said literatures merely indicate that the blood glucose level of the normal mice is decreased from the normal level (from about 100 mg/dl to about 80 mg/dl) by the intravenous injection of CNTF at the dose of 10 $\mu$g/kg, and the normal blood glucose level is decreased by transplantation of CNTF producing cells. This temporary decrease into the blood glucose level less than the normal level is caused by Cytokine IL-1-like effect as disclosed in said literature, which is considered to be substantially different from the effects of neurotrophic factors remarkably reducing the hyperglycemia in type II diabetic animal models, which is the essence of the present invention.

DISCLOSURE OF INVENTION

An object of the present invention is to provide a novel therapeutic agent for treating a patient of diabetes which can safely control the blood glucose level of the diabetic patient, and also to provide a novel therapeutic agent for treating a patient of hyperlipemia which can safely control the blood lipid level of the hyperlipemia patient. Especially, the present invention provides a therapeutic agent for treating a patient of diabetes which can cure type II diabetic mellitus accompanied by hyperglycemia caused by dysfunction of insulin activity, insulin resistance, reduction or failure of insulin secretion, glucose toxicity, hyperlipemia, obesity or hyperinsulinemia.

The present inventors have intensively studied the effects of neurotrophic factors which are peripherally administered to various diabetic animal models, and have found that the blood glucose level and the blood lipid level of spontaneously diabetic mice accompanied by hyperglycemia, obesity, insulin resistance, and hyperinsulinemia (one of type II diabetic model animals, C57 db/db mouse, Hitoshi ISHIDA et al., Saishin Igaku, vol. 48, p. 34 (1993)) can be reduced by administration of BDNF. Based on these findings further studies have been done, and as a result, the present invention has been accomplished.

That is, the present invention relates to the following medicaments.

(1) A therapeutic agent for treatment of a diabetes or a hyperlipemia, which comprises a neurotrophic factor as an active ingredient.

(2) A therapeutic agent according to the above (1), wherein the neurotrophic factor is a member selected from a neurotrophin family.
(3) A therapeutic agent according to the above (1), wherein the neurotrophic factor is a ligand of a trk or a p75 receptor.
(4) A therapeutic agent according to the above (1), wherein the neurotrophic factor is a ligand of a trkB or a trkC receptor.
(5) A therapeutic agent according to the above (1), wherein the neurotrophic factor is a brain-derived neurotrophic factor (BDNF).
(6) A therapeutic agent according to the above (1), wherein the neurotrophic factor is an NGF.
(7) A therapeutic agent according to the above (1), wherein the neurotrophic factor is an NT-3 or an NT-4/5.
(8) A therapeutic agent according to the above (1), wherein the neurotrophic factor is a CNTF.
(9) A therapeutic agent according to the above (1), wherein the neurotrophic factor is a GDNF.
(10) A therapeutic agent according to the above (1), wherein the neurotrophic factor is an HGF.
(11) A therapeutic agent according to any one of the above (1) to (10), wherein the diabetes is a non insulin dependent diabetes mellitus (type II, NIDDM).
(12) A therapeutic agent according to any one of the above (1) to (10), wherein the diabetes is a non insulin dependent diabetes mellitus, accompanied by a hyperglycemia, a hyperinsulinemia, a hyperlipemia, and/or an obesity.
(13) A therapeutic agent according to any one of the above (1) to (12), which exhibits its pharmacological activity through a humoral biologically active substance induced by a neurotrophic factor.
(14) A therapeutic agent for treatment of a hyperinsulinemia, which comprises a neurotrophic factor as an active ingredient.
(15) A therapeutic agent according to the above (14), wherein the hyperinsulinemia is accompanied by a Syndrome X, a Deadly quartet, or a visceral fat syndrome.
(16) A therapeutic agent for treatment of a hyperlipemia according to any one of the above (1)–(10), which is employed in the treatment of a hyperlipemia associating a diabetes.
(17) A therapeutic agent for treatment of a hyperlipemia according to any one of the above (1) to (10), which is employed in the treatment of a hyperlipemia associating an obesity.
(18) A therapeutic agent for treatment of a hyperlipemia according to any one of the above (1)–(10), which is the agent for treatment of a hypertriglyceridemia.

BEST MODE FOR CARRYING OUT THE INVENTION

Figure 1:
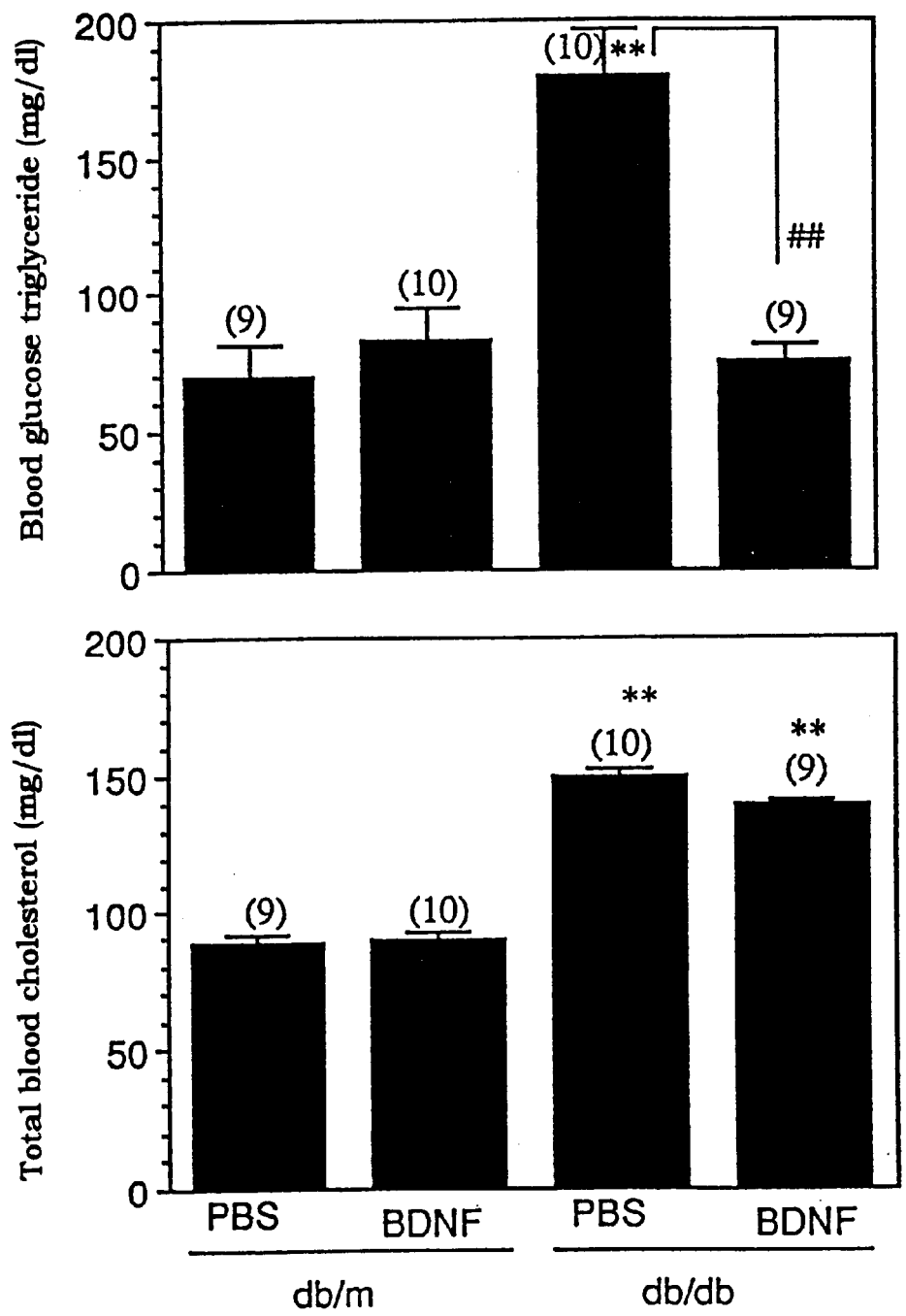
FIG. 1 shows the blood lipid controlling activity in db/db mice. The blood triglyceride level in the BDNF-treated group was significantly reduced in comparison with that of the PBS-treated group. Besides, the total blood cholesterol level was slightly decreased by BDNF administration.

The present invention is explained in more detail as follows.

In the present specification, the "neurotrophic factor" is a generic name for proteins, which exhibits biological activities such as an activity of maintaining the survival of neurons, or an activity of promoting the differentiation of neurons, such as a nerve growth factor (NGF) which was found in 1950. Specifically, the neurotrophic factors are, for example, a brain-derived neurotrophic factor (BDNF), an NGF, further a neurotrophin family comprising a neurotrophin 3 (NT-3), a neurotrophin 4/5 (NT-4/5), or a neurotrophin 6 (NT-6) (R. M. Lindsay et al.: TINS, vol. 17, p. 182 (1994) and R. M. Lindsay: Phil. Trans. R. Soc. Lond. B. vol. 351, p. 365–373 (1996)), moreover, a ciliary neurotrophic factor (CNTF), a glia-derived neurotrophic factor (GDNF), a glia growth factor (GGF2), a central nerve growth factor (AF-1), a hepatocyte growth factor (HGF) (A. Ebens et al., Neuron, vol. 17, p. 1157–1172 (1996)), etc. Moreover, biotechnologically engineered products of the above neurotrophic factors, which are derived by a partial substitution, an addition, a deletion or a removal by conventional genetic engineering techniques, are also included within the scope of the neurotrophic factors of the present invention as far as such product shows biological activities of the naturally-occurred neurotrophic factors.

The "neurotrophin" means a neurotrophic factor, which is secreted from the target cells for nerve growth, or promotes the growth, differentiation, or survival of neurons by autocrine or paracrine, and makes them form a neural circuit (synapse). For example, BDNF, NGF, NT-3, NT-4/5, and NT-6 are known at present, and they are a group of proteins having high homology of amino acid sequence and similar structure to each other. A new member of neurotrophins may be found in the future, and as disclosed in Examples of the present application, such a new neurotrophin can be evaluated on its pharmacological effects in a known experimental animal model, and should be included in the scope of the "therapeutic agent for treatment of diabetes" of the present invention. Among the neurotrophin family, the products of trk gene (e.g., trkA, trkB, trkC) being known as receptors for neurotrophins are useful, and BDNF, NT-3 and NT-4/5, which exhibit their biological effects through the products of trkB or trkC genes, i.e, trkB or trkC receptors, are most useful as a therapeutic agent for treatment of diabetes. "Diabetes" is a disease wherein the blood glucose level, which should usually be controlled at about 100–120 mg/dl, is abnormally raised. The blood glucose level of diabetes is, according to the present criterion of diagnosis for diabetes, is more than 200 mg/dl two hours after the tolerance test of glucose at the dose of 75 g, and more than 140 mg/dl of fasting blood glucose. In general, diabetes is classified into an insulin dependent diabetes mellitus (type I, IDDM) which is accompanied by reduction of insulin producing cells, and a non insulin dependent diabetes mellitus (type II, NIDDM), which is caused by insulin sensitivity reduction or insulin secretion reduction, and more than 90% of patients of diabetes are patients of the latter one. It has been considered that the cause of the former one is an insulitis, which may be caused by a virus infection or an autoimmunization under certain conditions, that is, insulin producing cells are destroyed by the inflammation of Langerhans islet of the pancreas, and whereby the absolute lack of insulin is induced. In many cases, type I diabetes mellitus breaks out acutely, and ketosis highly appears, and hence, continuous insulin injections are essential for life-support of the patients.

In a non insulin dependent diabetes mellitus (type II diabetes mellitus, NIDDM), ketosis less,appears, and the disease progresses slowly, and hence, insulin injections are not essentially necessary. It is considered that the onset of type II diabetes mellitus is caused by a genetic diathesis such as an insulin secretion dysfunction against glucose tolerance test, especially an insulin initial secretion disorder, and by further additional environmental factors such as obesity, hyperphagia, lack of exercise, and aging. On the other hand, it is alternatively considered that the genetic diathesis of impaired insulin action (insulin resistance) leads to the over-burden or exhaustion of the pancreas β cells, and further, environmental factors join thereto to cause type II diabetes mellitus.

Patients afflicted with the latter cases exist more in the Euro-American countries, and the blood insulin level therein is rather high (hyperinsulinemia), and many cases are associated with obesity. Any way, they are in the relative hypoinsulinemia conditions, and in the treatment of these diabetes patients, the treatment with insulin is not necessarily required, and the blood glucose level is mainly controlled by a dietary therapy or an exercise therapy. However, when the blood glucose level is not sufficiently controlled, then a drug, for example, a sulfonyl urea agent (SU agent) promoting the secretion of insulin, or a drug inhibiting the glucose-absorption at the small intestine, etc. is administered. However, an SU agent cannot be administered to treat a patient associated with obesity, and to such a patient, a biguanide agent or a newly commercially available drug which can suppress the insulin resistance may be administered. In either insulin dependent diabetes mellitus or non insulin dependent diabetes mellitus, when the blood glucose level cannot be sufficiently controlled to result in hyperglycemic conditions continuously, various diabetic complications such as a diabetic nephropathy, a diabetic retinopathy, a skin ulcer, a necrosis, a cardiovascular disorder, etc. supervene.

In the present invention and specification, a non insulin dependent diabetes mellitus of the young people, i.e., MODY (maturity-onset type of the diabetes in the young), an insulin receptor abnormalities, or a diabetes induced by abnormalities of genes of enzymes or other molecules related with the glucose metabolism such as insulin secretion or insulin activity are also included in type II diabetes mellitus of the present invention. Besides, a diabetes associates with abnormalities of a gene such as mitochondorion, which is considered to be a cause gene for type II diabetes mellitus while it is not yet clarified direct relation to glucose metabolism or mechanism of action of said gene, is also included in type II diabetes mellitus of the present invention. Moreover, a morbid hyperglycemia being caused by continuous administration of a steroid drug such as glucocorticoid (a steroid diabetes), or a hyperglycemia of Cushing Syndrome or an acromegaly is also included in type II diabetes mellitus because they are diabetes under normal or high level of insulin conditions.

The "therapeutic agent for treatment of hyperlipemia" means a drug reducing the level of blood lipid comprising triglyceride (neutral fat) or cholesterol of the patient afflicted with hyperlipemia by administration thereof.

The "hyperlipemia" is a disease wherein the abnormally high level of the blood lipid is sustained. From the present criteria for diagnosis of hyperlipemia, the fasting total blood cholesterol level is more than 220 mg/dl, and the fasting blood triglyceride level is more than 150 mg/ml. In general, hyperlipemia is known as a risk factor for an arteriosclerosis such as an ischemic heart disease, etc., and especially, the increase in LDL cholesterol and decrease in HDL cholesterol are considered to be most critical conditions. When LDL-C value is more than 100–160 mg/ml, and HDL value is less than 40 mg/ml, such condition is considered to be a subject to be treated by "a therapeutic agent for treatment of hyperlipemia". Hyperlipemia is caused by a genetic diathesis such as a familial hypercholesterolemia, or is caused by an obesity, or a hyperphagia or an epicurism. Moreover, the hyperlipemia is classified into a chylomicronemia (type I), a hyperchlorestorolemia (type IIa hyperlipemia), a hypertriglyceridema (type IV), or a combination thereof (type IIb or type III), etc., in terms of the symptoms thereof. The hyperlipemia of the present invention also includes all of these types as well.

The "blood glucose controlling activity" means an activity of reducing the blood glucose level of a diabetic patient, or an activity of maintaining it within the normal range. The "blood lipid controlling activity" means an activity of reducing the total blood cholesterol level or the total blood triglyceride level of hyperlipemia patients, or an activity of maintaining it within the normal range. The "tissue lipid accumulation controlling activity" means an activity of reducing the body weight of obesity patients by reducing the calorie intake or reducing the body fat accumulation.

The "insulin resistance" means a condition wherein the insulin level to be required to exhibit insulin activity at the same level as the healthy person is much higher than that of the healthy person. That is, it means a condition wherein the activity of insulin or sensitivity for insulin is reduced. The target organ for insulin activity includes a liver, a muscle (skeletal muscle), and an adipose tissue. In the present invention and specification, the peripheral organ is a liver, a muscle (skeletal muscle), or an adipose tissue, which is affected by insulin. Insulin exhibits a gluconeogenesis suppression activity, a glucose release suppression activity, etc. in the liver. Insulin exhibits glucose-uptake promoting activity in the muscle (skeletal muscle) and adipose tissues. The translocation of glucose transportation carrier called GLUT4 from the cytoplasma to the surface of the cell membrane is participated in the glucose-uptake. The clinical evaluation of insulin resistance includes, for example, euglycemic hyperinsulinemic clamp method.

The cause for insulin resistance is unknown, but the cause for insulin dysfuction in the peripheral tissues such as a liver, a muscle or an adipose tissue can be considered to be, for example, a disorder or an abnormality of signal transduction pathway through an insulin receptor, decrease in the expression of GLUT4 (glucose transportation carrier) being participated in glucose-uptake by insulin hormonal activity in the muscle and adipose tissues, decrease or abnormality of translocation of GLUT4 into the cell membrane, decrease in the glycogen synthesis in the muscle or liver, and enhancement of gluconeogenesis in the liver. A molecule which is a cause for insulin resistance is unknown, but it is suggested that a glucosamine, a low molecular G protein (RAD), a chyroinositol, a TNF-α, a free fatty acid, a membrane protein which is called as PC-1, etc. may be participated therein. The dysfunction of insulin activity induced by abnormality of insulin receptor genes is known as an insulin-receptor abnormalities.

The hyperglycemia being observed in diabetes mellitus is not simply an examination, but it is considered that hyperglycemia per se inhibits the insulin secretion, and exacerbates the insulin resistance. Thus, there is a "glucose-toxicity" theory that hyperglycemia per se is an important cause for diabetes which exacerbates the metabolism abnormality (edited by Takashi KADOWAKI, Molecular Medicine for Diabetes, published by Yodo Co. (1992)).

The "insulin resistance improving activity" means a pharmacological activity of antagonizing the change (increase of insulin resistance) caused by the sensitivity hebetation of cells against insulin, such as reduction of glucose-uptake into the peripheral tissues, enhancement of glucogenolysis, enhancement of gluconeogenesis, etc., which is observed in type II diabetes mellitus. When said pharmacological activity is exhibited, the blood glucose level is usually decreased, and the blood insulin level is reduced due to the living body feed-back system.

G. M. Raven proposed in 1988 a concept named Syndrome X, wherein arteriosclerosis may easily break out with being associated with an insulin resistance, a glucose tolerance reduction, a hyperinsulinemia, a hyper-VLDL-triglyceridemia, a hypo-HDL-cholesterolememia, and a hypertension (cf. G. M. Raven; Diabetes, vol. 37, p. 1595–1607 (1988)). In the symposium held at the 15th international Diabetes Society, there was a discussion based on a concept of "insulin resistance syndrome" wherein the onset of hyperinsulinemia based on insulin resistance leads to glucose tolerance reduction, hyper-VLDL-triglyceridemia, hypo-HDL-cholesterolemia and hypertension, and finally to cardiovascular disorders. In addition, N. M. Kaplan reported in 1989 that upper body obesity, glucose tolerance reduction, hypertriglyceridemia, and hypertension are called Deadly quartet, and patients associated with this Deadly quartet show a high rate of crisis of ischemic heart diseases (cf. N. M. Kaplan, Arch. Intern. Med. vol. 149, p. 1514–1520 (1989)). Moreover, Matsuzawa et al. disclosed that according to the study on obesity, they noted the relation between the fat distribution and the diabetic complications, and found that the visceral fat-type obesity wherein visceral fat (mesenterium fat, omental fat) accumulates within the abdomen is highly associated with glucose tolerance reduction, insulin resistance, hyperlipemia, cardiovascular disorders at a higher rate than the pannicule obesity is. Matsuzawa et al. also proposed visceral fat syndrome as a pathology wherein based on the visceral fat accumulation, multiple risk factors such as glucose tolerance reduction, hyperlipemia, hypertension, etc., simultaneously exist, and then these factors easily lead to arteriosclerosis (Tadashi NAKAMURA et al., the Report of the 12th Japan Bariatorics Society, p. 161–162 (1992); Shigenori FUJIOKA, Yuji MATSUZAWA, Progress in Molecular Diabetology, p. 145–151 (1994), etc.). Some concepts as mentioned above are correlated to each other, and in addition to the above nomenclatures, they are also named by other nomenclatures according to the westernized diet, for example, Coca-colanization, Acculturation, Modernization, Westernization, etc., which are called New Word Syndrome. As disclosed in Examples of the present invention and specification, neurotrophic factors are useful in the prophylaxis or treatment of the syndromes, diseases, and pathologies of the above-mentioned concepts.

In the present specification, "hyperinsulinemia" means a generic name for pathologies wherein the blood insulin level is higher than the normal level. "Syndrome X" means syndromes wherein insulin resistance, glucose tolerance reduction, hyperinsulinemia, hyper-VLDL-triglyceridemia, hypo-HDL-chloresterolemia, and hypertension are all associated, and arteriosclerosis may easily break out. "Deadly quartet" means pathologies being accompanied by upper body obesity, impaired glucose tolerance, hypertriglyceridemia, and hypertension. "Visceral fat syndrome" means pathologies wherein visceral fat in the abdomen (mesenterium fat, omental fat) accumulates, and based on the visceral fat accumulation, multiple risk factors such as impaired glucose tolerance, hyperlipemia, hypertension, etc. exist simultaneously, and as a result, arteriosclerosis may easily break out.

"Humoral biologically active substance induced by a neurotrophic factor" means biologically active substances which are induced in the living body of an animal to be administered by a neurotrophic factor, and released into the peripheral bloodstream, and which exhibit a blood glucose controlling activity, a blood lipid controlling activity, body fat accumulation controlling activity, or an insulin resistance improving activity.

METHOD FOR PREPARATION

A neurotrophic factor used for treatment of diabetes or hyperlipemia of the present invention may be any one, for example, naturally-occurred ones, gene recombinant ones, as far as they show their inherent biological activities, and can be used in the present invention with purification. The detailed procedures of preparing thereof are explained below.

METHOD FOR PREPARATION OF BDNF:

A BDNF was isolated from porcine brain by Brade, Y. E. et al (cf. The EMBO Journal, vol. 5, p. 549–553 (1982)), and BDNF genes was analyzed after cloning whereby it was confirmed that BDNF has a primary structure consisting of 119 amino acids (cf., Leibrock, J. et al., Nature, vol. 341, p. 149 (1989)), but a modified recombinant BDNF such as Met-BDNF having a methionine residue at the N-terminus, or a recombinant BDNF produced by an addition, a substitution, a deletion or a removal of a part of amino acid sequence of a natural BDNF by a conventional gene engineering technique may be used in the present invention, as far as they are a pharmaceutical preparation having a BDNF activity.

The "BDNF activity" means in the present invention an activity of maintaining survival or promoting differentiation of a dorsal root ganglia, a ganglion inferius nervi vagi, a motoneuron, a retina ganglia, a nigradopaminergic neuron, a basal forebrain cholinergic neuron, etc. These activities in the living body can be confirmed in vitro or in vivo (Japanese Patent Publication No. 5-328974, U.S. Pat. No. 5,180,820).

Various methods for preparing BDNF have been reported, and any BDNF which is prepared by any method can be used in the present invention. When a BDNF isolated from animal tissues is used in the present invention, it may be purified to such a degree that it can be used as a medicament (cf., The EMBO Journal, vol. 5, p. 549–553 (1982)). Alternatively, a BDNF can be obtained by culturing a primary culture cell or an established cell line that can produce BDNF, and isolating from the culture broth thereof (e.g., culture supernatant, cultured cells). Moreover, there may be used a recombinant BDNF which can be obtained by a conventional gene engineering technique, e.g., by inserting a gene encoding BDNF into a suitable vector, transforming a suitable host with the recombinant vector, and isolating from a culture supernatant of the resulting transformant (cf., Proc. Natl. Acad. Sci. USA, vol. 88, p. 961 (1991); Biochem. Biophys. Res. Commun., vol. 186, p. 1553 (1992)), which is suitable for production of BDNF of uniform property in a large scale. The host cells to be used in the above process is not limited, but may be any conventional host cells which have been used in a gene engineering technique, for example, *Escherichia coli, Bacillus subtilis*, yeasts, plant cells or animal cells.

METHOD FOR PREPARATION OF NGF:

An NGF can be prepared by expressing in various host cells in the same manner as in the preparation of BDNF. In cases that an animal cell is used as a host cell (CHO cell, Schmelzer, C. H.: J. Neurochemistry, 59, 1675–1983 (1992)), or in cases that a procaryotic cell is used as a host cell (*E. coli* cell, Japanese Patent No. 2637392), the methods being able to give active NGF are established in both cases.

METHOD FOR PREPARATION OF NT-3:

An NT-3 can be prepared by expressing in various host cells in the same manner as in the preparation of BDNF. The methods for preparing thereof and the methods for assay thereof are disclosed in Neuron, vol. 4, 767–773 (1990), or Japanese Patent Publication No. 5-161493 (WO 91/3659).

METHOD FOR PREPARATION OF NT-4:

An NT-4 can be prepared by expressing in various host cells in the same manner as in the preparation of BDNF. The methods for expression of the recombinant NT-4 and the methods for assay thereof are disclosed in Proc. Natl. Acad. Sci. USA, vol. 89, p. 3060–3064 (1992.4), Japanese Patent Publication No. 4-509600 (WO 93/25684), or Japanese Patent Publication No. 6-501617 (WO 92/5254).

METHOD FOR PREPARATION OF CNTF:

A CNTF can be prepared in a large scale by expressing in various host cells in the same manner as in the preparation of BDNF. The methods for expression of the recombinant CNTF and the methods for assay thereof are disclosed in Biochimica et Biochimica Acta, vol. 1090, p. 70–80 (1991), J. Neurochemistry, vol. 57, p. 1003–1012 (1991). The methods for preparing the recombinant CNTF and the purification thereof are disclosed in Japanese Patent Publication No. 4-502916 (WO 90/7341).

METHOD FOR PREPARATION OF GDNF:

A GDNF can be prepared by expressing in various host cells in the same manner as in the preparation of BDNF. The methods for preparing GDNF are disclosed in Science, vol. 260, p. 1130–1132 (1993.5), WO 97/19694, WO 97/19695.

METHOD FOR PREPARATION OF HGF:

An HGF can be prepared by expressing in various host cells in the same manner as in the preparation of BDNF. For example, a recombinant HGF can be obtained and its activity can be evaluated by the method disclosed in Nature, vol. 342, 440 (1989), Japanese Patent Publication No. 5-111383, Japanese Patent Publication No. 4-30000.

PHARMACEUTICAL PREPARATION

A pharmaceutical preparation of the above-mentioned various neurotrophic factors may be a parenteral injection preparation, an oral preparation, a liquid preparation, a lyophilized preparation, but the parenteral injection preparation for subcutaneous administration are preferable. These pharmaceutical preparations may contain a conventional stabilizer or a carrier used in this field (techniques for medical protein preparations), for example, a protein derived from the serum such as albumin, an amino acid such as glycine, a saccharide such as mannitol, etc., and can be used in the lyophilized preparation suitable for subcutaneous, intravenous or intramuscular administration. Besides, when a pharmaceutical preparation of the present invention is in the form of a solution preparation or a lyophilized preparation, a surfactant such as Tween 80 is preferably added thereto in order to prevent aggregation of an active substance. When a prolonged pharmacological effect is required, then it is possible to prepare a pharmaceutical preparation with using a conventional protein sustained-release pharmaceutical carrier.

USAGE

Usage of the agent for treatment of diabetes or hyperlipemia of the present invention is explained below.

USAGE OF BDNF:

When an active ingredient is a BDNF, the daily dosage thereof is in the range of 0.01 µg–100 mg per 1 kg of the body weight in an adult, preferably in the range of 0.1 μg–1 mg/kg, and it can be administered intravenously, subcutaneously, intracutanously or intramuscularly. The frequency of the administration may vary according to the dosage, administration route, or conditions of the patients, and is not critical, but it is possibly in the range of once a month to three times a day, for one day to about 9 months. By the treatment by BDNF, the blood glucose level, the blood lipid level and the body fat (body weight) can be reduced to give a suitable blood glucose level and a reduced and stable blood lipid level. An agent of the present invention having a rapid pharmacological activity can probably be administered together with daily diet before meal in order to suppress the hyperglycemia after meal, or a therapeutic agent of the present invention having a durable activity can probably be administered in order to enhance the insulin activity of basal secretion during the fasting between meals or during the sleeping.

USAGE OF NGF:

When an active ingredient is an NGF, the daily dosage thereof is usually in the range of 0.01 μg–10 mg per 1 kg of the body weight in an adult, preferably in the range of 0.1 μg–1 mg/kg, and it can be administered intravenously, subcutaneously, or intramuscularly. An NGF is considered to be required in higher dose in order to exhibit the hypoglycemic activity than other neurotrophic factors. That is, in the animal tests, other neurotrophic factors exhibited their effectiveness at a dose of 20 mg/kg, while an NGF exhibiting its pharmacological activity through trkA receptors did not exhibit its effectiveness at the same dose, but showed its pharmacological activity at a dose of 100 mg/kg.

USAGE OF NT-3:

When an active ingredient is an NT-3, the daily dosage thereof is usually in the range of 0.01 μg–40 mg per 1 kg of the body weight in an adult, preferably in the range of 0.1 μg–1 mg/kg, and it can be administered intravenously, subcutaneously, or intramuscularly.

USAGE OF NT-4:

When an active ingredient is an NT-4, the daily dosage thereof is usually in the range of 0.01 μg–40 mg per 1 kg of the body weight in an adult, preferably in the range of 0.1 μg–1 mg/kg, and it can be administered intravenously, subcutaneously, or intramuscularly.

USAGE OF CNTF:

When an active ingredient is a CNTF, the daily dosage thereof is usually in the range of 0.01 μg–40 mg per 1 kg of the body weight in an adult, preferably in the range of 0.1 μg–1 mg/kg, and it can be administered intravenously, subcutaneously, or intramuscularly.

USAGE OF GDNF:

When an active ingredient is a GDNF, the daily dosage thereof is usually in the range of 0.01 μg–40 mg per 1 kg of the body weight in an adult, preferably in the range of 0.1 μg–1 mg/kg, and it can be administered intravenously, subcutaneously, or intramuscularly.

USAGE OF HGF:

When an active ingredient is an HGF, the daily dosage thereof is usually in the range of 0.01 μg–40 mg per 1 kg of the body weight in an adult, preferably in the range of 0.1 μg–1 mg/kg, and it can be administered intravenously, subcutaneously, or intramuscularly.

MECHANISM OF ACTIVITY

A hypoglycemic activity and an activity of treating hyperlipemia of neurotrophic factors cannot be explained from conventional findings, but at least, it is considered that such activities of neurotrophic factors are completely different from activities of insulin or IGF, or an HGM-CoA reductase inhibitor (pravastatin, simvastatin), or colestryramine inhibiting enterohepatic circulation of bile acid, or a fibrate agent or a nicotinic acid agent, and it is considered to be a quite new mechanism.

The mechanism of anti-diabetic activity of neurotrophic factors is unclear, however, it can be considered as described below. First, there is a possibility of acting on nerve cells, especially through trk, p75 receptors, etc., and a possibility of acting through receptors including trk or p75 existing in non-nerve cells. There are other possibilities of directly acting by the stimulus of these receptors, or indirectly acting through another second vital molecule. The affected area could be three parts such as (1) central nerve, e.g., hypothalamus, or hypophysis, (2) peripheral tissues, e.g., muscle, fat, liver, etc., and (3) pancreas producing insulin. First, there is a regulating activity of bio-homeostasis, which maintains the blood glucose through hypothalamus or hypophysis, etc. In the peripheral tissues as above (2), reduction or complete cure of insulin resistance can occur. In the pancreas, there could be effects on glucagon. Since there were observed expedited effects in addition to delayed effects, it can be considered that an unstable active substance or a humoral biologically active substance, which is the second active substance, can possibly be induced by administration of a neurotrophic factor.

TOXICITY AND SIDE EFFECTS

BDNF:

BDNF was administered subcutaneously to rats and cynomolgus monkeys at a dose of 100 mg/kg and 60 mg/kg, respectively, for four weeks, but no animal was dead. With respect to the acute toxicity, BDNF was administered to rats and cynomolgus monkeys at a dose of more than 200 mg/kg, and no animal was dead. Therefore, BDNF shows high safety. Besides, when BDNF was administered to normal animals such as rats, the blood glucose level of the animals was not reduced. Therefore, it is considered that BDNF does not cause hypoglycemia. When BDNF was administered to normal animals that had been fasted overnight, the blood glucose level thereof was not reduced.

NGF:

It is reported that when NGF was administered once by intravenous (i.v.) or subcutaneous (s.c.)injection at a dose of more than 0.1 μg/kg, NGF gave a muscle ache to a normal volunteer, but there was observed no serious side effect which may lead to death even at the highest dose 1 μg/kg (Ann. Neurol., vol. 36, p. 244–246 (1994)). Besides, effects on sensory nerve dysfunction of NGF have been studied with administering to rats at a dose of 5 mg/kg of NGF (s.c.), three times a weak, for 14 weeks (Brain Research, vol. 634, p. 7–12 (1994)). It is clear that the daily dose in NGF of mg/kg order is not a lethal dose of rat.

CNTF:

When CNTF was administered to patients afflicted with Amyotrophic lateral sclerosis (ALS) by subcutaneous injection at a dose of 0.5 to 30 μg/kg/day, three times a week, for two weeks, the patients showed fever, dry cough, or tiredness at a dose of 30 μg/kg (Clinical Neuropharmacology, vol. 18, p. 515–532 (1995)), however, no fatal side effect was observed at said dose. In addition, when CNTF was daily administered subcutaneously to patients afflicted with ALS at a dose of 2–100 μg/kg, a patient having anamnesis showed herpes stomatitis, which was considered to be caused by a high dose (more than 10 μg), and also showed inappetency, loss of body weight, and cough (Neurology, vol. 47, p. 1329–1331 (1996)).

NT-3, NT-4, GDNF and HGF:

Each of these neurotrophic factors does not show side effects which may lead to death, or toxicity, like BDNF.

The present invention is illustrated by Examples.

PREPARATIONS

Among the preparations of neurotrophic factors of the present invention, the aqueous solution preparation and lyophilized preparation for subcutaneous administration of the representative one, BDNF, are prepared as follows.

(1) To a purified recombinant BDNF (1 mg) were added glycine (0.34 mg), mannitol (9 mg), and non-ionic surfactant, Polysolvate 80 (0.2 mg), and the mixture was dissolved in a 5 mM phosphate buffer (pH 7.4, 1 ml), and lyophilized.

(2) BDNF was dissolved in a 10 mM phosphate buffer (pH 7.0) containing 150 mM sodium chloride and 0.01% Tween 80 so that the concentration of BDNF was adjusted to 5 mg/ml, to give a BDNF aqueous solution.

(3) BDNF was dissolved in 10 mM phosphate buffer (pH 7.0) containing 150 mM sodium chloride and 0.01% Tween 80 so that the concentration of BDNF was adjusted to 5 mg/ml. Subsequently, to the mixture was added mannitol so that the concentration of mannitol is 10 mg/ml to give a BDNF aqueous solution. The mixture was put into vials aseptically, and lyophilized to give a lyophilized preparation of BDNF. Nitrogen gas was purged into the vials, and the vials were sealed.

EXAMPLE 1

PHARMACOLOGICAL EXPERIMENT

Blood Glucose Controlling Activity in db/db Mice

Non insulin dependent diabetes mice (db/db mice), (male, 10 weeks old, 10 mice/group) were freely fed, and to the mice was administered BDNF 20 mg/kg once a day, 5 days a week, for 8 weeks (subcutaneous administration). The blood was taken out before and 4 weeks and 8 weeks after the administration from the tail vein, and the glucose level therein was measured with a Tide blood glucose assay kit (hexokinase method, Bayer-Sankyo). The collection of the blood before the administration was carried out under free feeding, and the collection of the blood 4 or 8 weeks after the administration was carried out after 24 hours fasting, and PBS (phosphate buffered saline solution) was given to the control group.

The results using BDNF are shown in Table 1. Difference between the BDNF-treated group and the control group was analyzed by Student's t-test.

TABLE 1

| | Blood glucose level | | |
|---|---|---|---|
| | Value before administration | 4 weeks after administration | 8 weeks after administration |
| Control group | 386 ± 24 | 335 ± 36 | 290 ± 34 |
| BDNF-treated Group | 395 ± 27 | 170 ± 18* | 114 ± 8** |

**P < 0.01
*P < 0.05

As shown in Table 1, the blood glucose level was dramatically reduced in the BDNF-treated group to almost normal level, in comparison with that of the control group. Moreover, the blood glucose reducing activity in the db/db mice is characteristic because this activity does not reduce the blood glucose level of the normal mice (db/m mice) to less than the normal level, which is preferable characteristic, while a conventional oral antidiabetic agent often causes hypoglycemia. In addition, since the food intake was decreased in the BDNF-treated group, the food intake in the control group was also decreased to the same intake of the BDNF-treated group (Pair Feeding), the similar result of the difference between the blood glucose levels was also observed, and hence, the blood glucose controlling activity of BDNF is considered not to depend on the decrease in the food intake.

EXAMPLE 2

PHARMACOLOGICAL EXPERIMENT

Blood Lipid Controlling Activity of BDNF in db/db Mice db/db Mice (female, 7 weeks old, 9–10 mice/group), which spontaneously showed hyperglycemia and hyperlipemia, were freely fed, and to the mice was subcutaneously administered PBS (phosphate buffered saline solution) or BDNF (20 mg/kg) once a day, 7 days a week, for 2 weeks. About 24 hours after the last administration, the blood was taken out from the mice at the tail vein under free feeding, and the lipid level in plasma was measured. The blood triglyceride level was measured with a triglyceride assay kit, Triglyceride G-Test Wako, manufactured by Wako Pure Chemical Industries, Ltd., and the total blood cholesterol level was measured with a total cholesterol assay kit, Cholesterol E-Test Wako, manufactured by Wako Pure Chemical Industries, Ltd. The blood lipid level of db/m mice that did not show hyperlipemia was considered to be the standard level for normal healthy animals.

The results of the experiment are shown in FIG. 1. The blood lipid in the PBS-treated db/db mice was raised to about 180 mg/dl of triglyceride, and 150 mg/dl of total cholesterol, which were higher than those of the db/m mice by about 2.5 times, and about 1.7 times, respectively. On the other hand, in the BDNF-treated group, the increase in the blood lipid level was significantly suppressed, especially the increase in the blood triglyceride level was significantly suppressed to about 75 mg/dl of triglyceride (Student' t-test). The total cholesterol level was slightly reduced to 138 mg/dl.

EXAMPLE 3

PHARMACOLOGICAL EXPERIMENT

Anti-obesity Activity of BDNF in db/db Mice db/db Mice (female, 7 weeks old, 9–10 mice/group), which spontaneously showed hyperglycemia and obesity, were freely fed, and to the mice was daily subcutaneously administered PBS (phosphate buffered saline solution) or BDNF (20 mg/kg) once a day for 4 weeks. The body weights of the mice were measured at 7th day, 14th day, and 28th day before the daily administration of BDNF.

Figure 2:
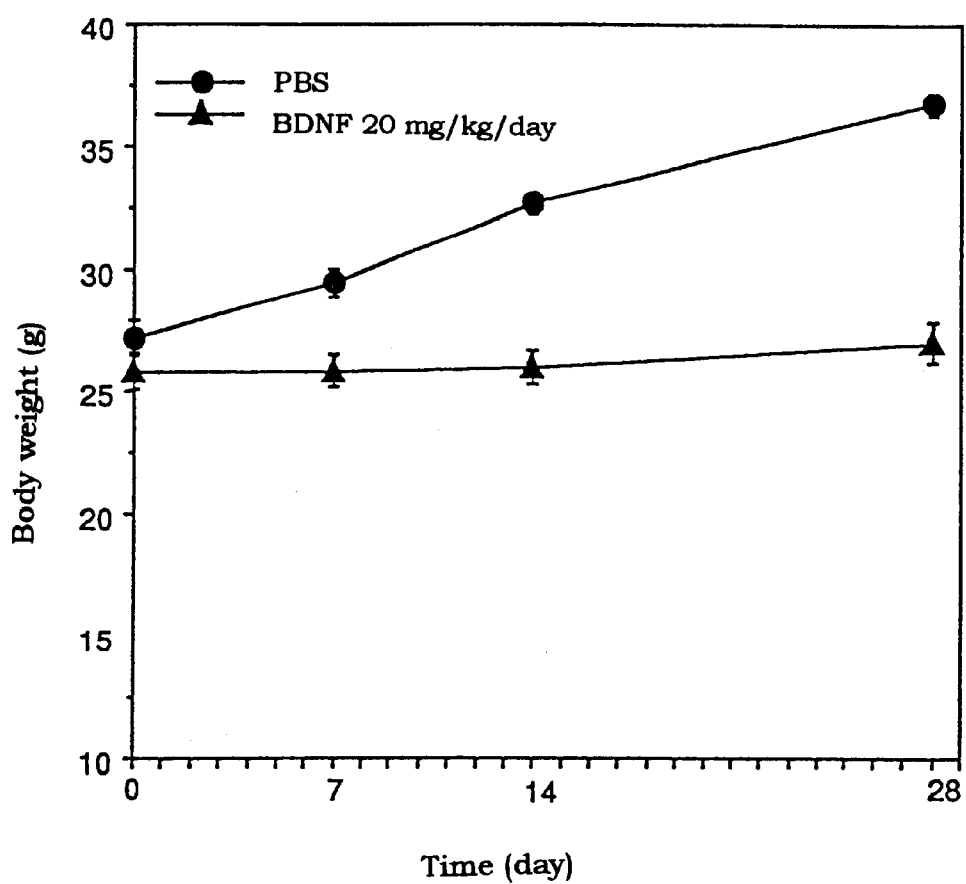
FIG. 2 shows the anti-obesity activity in db/db mice. The body weight in the BDNF-treated group was not increased and obesity was suppressed, in comparison with those of the PBS-treated group.

The results of the experiment are shown in FIG. 2. The body weight in the PBS-treated group was increased by 10 g (27 g→37 g), while the body weight of the BDNF-treated group was merely increased by about 1 g or less, and the obesity was not observed (25 g→26 g).

EXAMPLE 4

PHARMACOLOGICAL EXPERIMENT

Insulin Resistance Improving Activity of BDNF in db/db Mice db/db Mice (female, 7 weeks old, 9–10 mice/group), which spontaneously showed hyperglycemia and hyperinsulinemia, were freely fed, and to the mice was daily subcutaneously administered PBS (phosphate buffered saline solution) or BDNF (20 mg/kg) once a day, for 4 weeks. About 24 hours after the last administration, the blood was taken out from the mice at the tail vein under free feeding, and the insulin level in the plasma was measured. The blood insulin level was measured with a kit for measuring insulin, manufactured by Morinaga Bioscience Institute, Ltd. The blood insulin level of db/m mice that did not show hyperinsulinemia was considered to be the standard insulin level for normal healthy animals.

Figure 3:
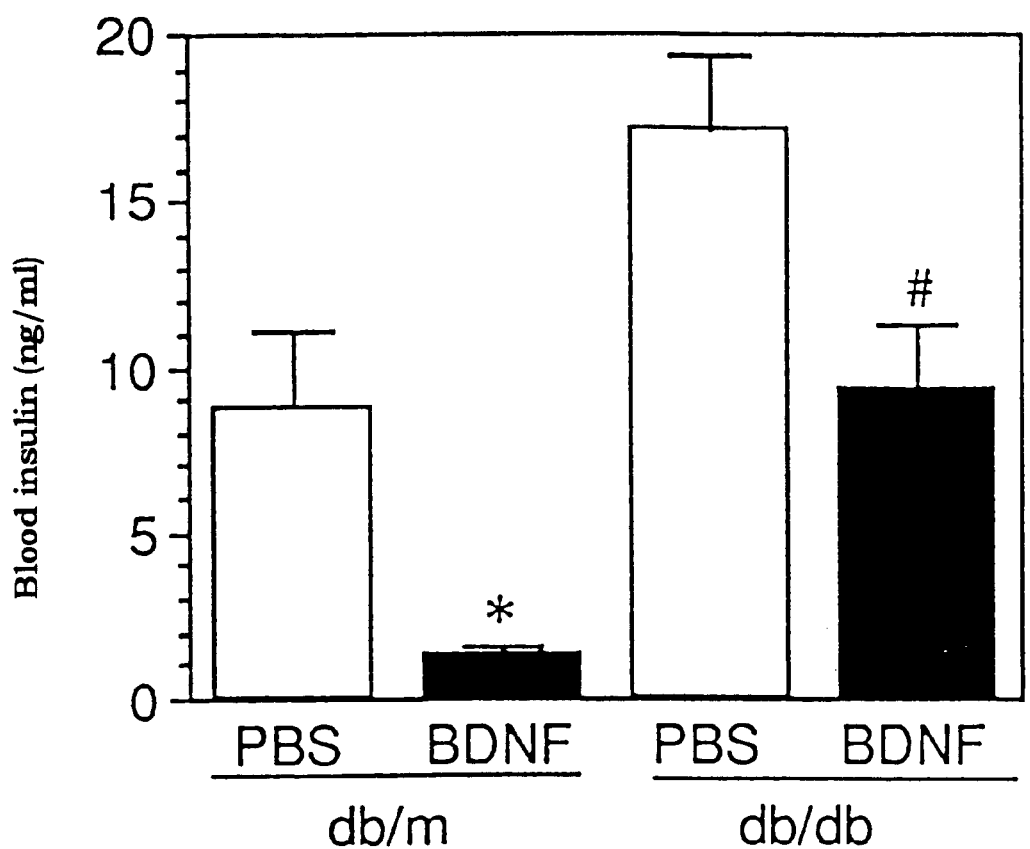
FIG. 3 shows the insulin resistance improving activity in db/db mice. The blood insulin level was significantly decreased in the BDNF-treated group, in comparison with that of the PBS-treated group.

The results of the experiment are shown in FIG. 3. The blood insulin in the PBS-treated db/db mice was raised to about 17 ng/ml, while in the BDNF-treated group, the increase in the blood insulin level was significantly suppressed to about 9 ng/ml (Student' t-test).

Even though the insulin level in the BDNF-treated group was reduced in comparison with the control group, the blood glucose level therein was also reduced, and hence, it can be considered that the insulin resistance in the db/db mice was improved in the BDNF-treated group.

EXAMPLE 5

PHARMACOLOGICAL EXPERIMENT

Blood Glucose Controlling Activity of Neurotrophic Factor in db/db Mice

Non insulin dependent diabetic mice (db/db mice) (female, 7 weeks old, 3–4 mice/group) were freely fed, and to the mice was subcutaneously administered a neurotrophic factor at a dose of 20 mg/kg to 100 mg/kg. The blood was taken out from the mice at the tail vein before the administration of a neurotrophic factor, and 1, 2, 3, 4, 6 hours after the administration of a neurotrophic factor, and the glucose level therein was measured with Antsense II (immobilized enzyme membrane/hydrogen peroxide electrode method, Bayer·Sankyo). The group treated with PBS (phosphate buffered saline solution) was considered as the control group.

The results are shown in Table 2. Difference between the blood glucose levels before and after the administration were analyzed by Student' t-test or Welch's test. The following various neurotrophic factors were used. BDNF (REGENERON PHARMACEUTICALS, INC.), CNTF (REGENERON PHARMACEUTICALS, INC.), HGF (Sumitomo Pharmaceuticals Company, Limited), NT-3 (Pepurotech), GDNF (Pepurotech), and NGF (Serotech).

TABLE 2

|  | PBS | BDNF 20 mg/kg | CNTF 20 mg/kg | HGF 20 mg/kg | NGF 100 mg/kg |
|---|---|---|---|---|---|
| 0 hour | 305 ± 87 | 280 ± 18 | 252 ± 35 | 266 ± 27 | 286 ± 42 |
| 1 hours | 272 ± 85 | 212 ± 43 | 178 ± 18 | 156 ± 10* | 213 ± 23 |
| 2 hours | 298 ± 54 | 188 ± 5** | 121 ± 14* | 195 ± 22 | 217 ± 28 |
| 3 hours | 251 ± 65 | 171 ± 13** | 139 ± 5 | 226 ± 15 | 262 ± 32 |
| 4 hours | 335 ± 81 | 196 ± 24** | 148 ± 10* | 201 ± 33 | 181 ± 12 |
| 6 hours | 402 ± 31 | 236 ± 28 | 126 ± 15* | 254 ± 59 | 180 ± 17 |

|  | PBS (n = 3) | NT-3 20 mg/kg (n = 4) | GDNF 20 mg/kg (n = 4) |
|---|---|---|---|
| 0 hour | 351 ± 64 | 356 ± 40 | 356 ± 38 |
| 1 hours | 356 ± 61 | 253 ± 23 | 261 ± 14 |
| 2 hours | 324 ± 61 | 212 ± 13* | 261 ± 33 |
| 3 hours | 395 ± 59 | 172 ± 8* | 308 ± 29 |
| 4 hours | 315 ± 37 | 165 ± 6* | 188 ± 21* |
| 6 hours | 388 ± 77 | 152 ± 9* | 157 ± 12** |

All n = 3
*P < 0.05,
**P < 0.01 vs. 0 hour (Student' or Welch's t-test)
*P < 0.051,
**P < 0.01 vs. 0 hour (Student' or Welch's t-test)
Every value indicates the average blood glucose level (mg/dl) ± standard error

INDUSTRIAL APPLICABILITY

As mentioned above, the hypoglycemic agent of the present invention exhibits, in addition to the blood glucose controlling activity, the blood lipid controlling activity, the body fat accumulation controlling activity, and the insulin resistance improving activity, and hence, they can treat all of hyperilipemia, or diabetes associated with obesity or hyperinsulinemia.

What is claimed is:

1. A method for controlling blood glucose levels in a mammal or patient having non-insulin dependent diabetes mellitus comprising:

administering a therapeutic agent comprising an effective amount of a hepatocyte growth factor to the mammal or patient in need thereof.

2. A method for controlling blood lipid levels in a mammal or patient having non-insulin dependent diabetes mellitus comprising:

administering a therapeutic agent comprising an effective amount of a hepatocyte growth factor to the mammal or patient in need thereof.

3. The method according to claim 1 or 2, wherein the effective amount is 0.01 µg/kg to 40 mg/kg by weight of the mammal or patient.

4. The method according to claim 1 or 2, wherein the therapeutic agent is administered subcutaneously, intravenously or intramuscularly.

* * * * *